US010350053B2

(12) United States Patent
Kumar

(10) Patent No.: US 10,350,053 B2
(45) Date of Patent: Jul. 16, 2019

(54) MUSCLE TISSUE ANCHOR PLATE

(71) Applicant: Avinash Kumar, Lakewood Ranch, FL (US)

(72) Inventor: Avinash Kumar, Lakewood Ranch, FL (US)

(*) Notice: Subject to any disclaimer, the term of this patent is extended or adjusted under 35 U.S.C. 154(b) by 385 days.

(21) Appl. No.: 14/882,764

(22) Filed: Oct. 14, 2015

(65) Prior Publication Data

US 2016/0100932 A1 Apr. 14, 2016

Related U.S. Application Data

(60) Provisional application No. 62/063,430, filed on Oct. 14, 2014.

(51) Int. Cl.
*A61F 2/08* (2006.01)
*A61B 17/80* (2006.01)
*A61B 17/04* (2006.01)

(52) U.S. Cl.
CPC ........ *A61F 2/0811* (2013.01); *A61B 17/0401* (2013.01); *A61B 17/80* (2013.01); *A61B 17/8061* (2013.01); *A61B 2017/044* (2013.01); *A61B 2017/0445* (2013.01); *A61F 2002/0852* (2013.01)

(58) Field of Classification Search
CPC .................. A61F 2/0811; A61B 17/80–826
See application file for complete search history.

(56) References Cited

U.S. PATENT DOCUMENTS

| 5,571,139 | A | * | 11/1996 | Jenkins, Jr. | ........ | A61B 17/0401 606/232 |
| 6,096,040 | A | * | 8/2000 | Esser | ................. | A61B 17/8061 606/280 |
| 6,139,550 | A | * | 10/2000 | Michelson | ......... | A61B 17/1604 606/287 |
| 6,139,565 | A | * | 10/2000 | Stone | ................. | A61B 17/0401 606/232 |
| 6,149,653 | A | * | 11/2000 | Deslauriers | ........ | A61B 17/0401 606/232 |
| 6,436,124 | B1 | * | 8/2002 | Anderson | .......... | A61B 17/0401 606/232 |
| 8,088,130 | B2 | * | 1/2012 | Kaiser | ................. | A61B 17/0401 606/139 |
| 8,119,152 | B2 | * | 2/2012 | Shikinami | ............. | A61L 27/446 424/424 |
| 8,231,654 | B2 | * | 7/2012 | Kaiser | ................. | A61B 17/0401 606/232 |

(Continued)

*Primary Examiner* — Zade Coley
(74) *Attorney, Agent, or Firm* — Dinsmore & Shohl LLP

(57) ABSTRACT

A plate for use in the repair of a torn tendon or ligament and a method for using said plate are provided. The plate includes a plurality of screw holes. The plate also includes a suture anchor point disposed on the plate body. The plate further includes a porous portion configured to allow muscle tissue to migrate through the porous portion and into the bone as the tissue regrows. The method includes the step of securing the plate to a bone by inserting a bone screw and anchor screw(s) through the screw holes. The method proceeds to the step of sewing the sutures to the damaged tendon/ligament and securing the suture to the suture anchor point. Wherein the damaged tendon/ligament is attached to the plate, and wherein muscle tissue may migrate through the porous portion and into the bone as the tissue regrows.

9 Claims, 7 Drawing Sheets

(56) References Cited

U.S. PATENT DOCUMENTS

| | | | |
|---|---|---|---|
| 8,668,723 B2* | 3/2014 | Altarac | A61B 17/7059 606/290 |
| 2002/0183754 A1* | 12/2002 | Michelson | A61B 17/7058 606/70 |
| 2005/0015088 A1* | 1/2005 | Ringeisen | A61B 17/80 623/11.11 |
| 2005/0234458 A1* | 10/2005 | Huebner | A61B 17/8061 606/71 |
| 2005/0240187 A1* | 10/2005 | Huebner | A61B 17/80 606/71 |
| 2006/0041262 A1* | 2/2006 | Calvert | A61B 17/80 606/76 |
| 2006/0052782 A1* | 3/2006 | Morgan | A61B 5/076 606/60 |
| 2008/0188936 A1* | 8/2008 | Ball | A61B 17/1146 623/13.14 |
| 2008/0300637 A1* | 12/2008 | Austin | A61B 17/74 606/290 |
| 2009/0062848 A1* | 3/2009 | Ken | A61B 17/0057 606/213 |
| 2009/0088808 A1* | 4/2009 | Lindemann | A61B 17/7059 606/286 |
| 2009/0118776 A1* | 5/2009 | Kelsch | A61B 17/0401 606/325 |
| 2009/0138082 A1* | 5/2009 | Reah | A61B 17/7059 623/13.14 |
| 2009/0177230 A1* | 7/2009 | Henderson, Sr. | A61B 17/7055 606/246 |
| 2010/0016899 A1* | 1/2010 | Gelfand | A61B 17/0401 606/280 |
| 2010/0100127 A1* | 4/2010 | Trenhaile | A61B 17/0401 606/232 |
| 2011/0160856 A1* | 6/2011 | Sinnott | A61B 17/0487 623/13.14 |
| 2013/0226204 A1* | 8/2013 | Kumar | A61B 17/0487 606/151 |
| 2014/0052177 A1* | 2/2014 | Singhatat | A61B 17/842 606/232 |

* cited by examiner

MUSCLE TISSUE ANCHOR PLATE

CROSS-REFERENCE TO RELATED APPLICATIONS

This application claims priority of U.S. Provisional Application 62/063,430 filed Oct. 14, 2014, the contents of which are incorporated herein by reference.

FIELD OF THE INVENTION

The present invention is related to a plate configured to assist in the repair of muscle tissue, the plate includes a suture anchor point configured to receive sutures so as to secure the sutures to the plate, and a method of repairing muscle tissue using said plate.

BACKGROUND OF THE INVENTION

Current surgical techniques to repair muscle tissue utilizes one or more screws secured directly to a patient's skeletal structure. The screws were used as anchors enabling sutures to be attached to the screw, sewn onto the damaged tissue and then attached back onto the respective anchor. Thus, there remains a single point of securement. An alternate technique improved this method by including a reinforcing mesh over the damaged tissue, with the mesh sutured to both the anchors and surrounding muscle tissue. The mesh helps to distribute stress throughout the muscle tissue and increase viability of repairs. However, the mesh may fail as the mesh is secured to only a single screw point.

In particular procedures may be subject to failure in instances where the bone is porous, suffers from osteoporosis or cystic changes as the screws become loose. Accordingly, it remains desirable to have a device configured to distribute the load among multiple locations of the bone so as to reduce the effects of osteoporosis or cystic changes.

SUMMARY OF THE INVENTION

A plate for use in the repair of muscle tissue such as a torn tendon or ligament is provided. The plate includes a plurality of screw holes for accepting screws. One of the screw holes is a bone screw hole configured to receive a bone screw. The other screw holes is an anchor screw hole configured to receive anchor screws. The anchor screws include suture fixedly attached thereto.

The plate includes a porous portion surrounding the anchor screw holes. The porous portion is configured to allow muscle tissue to migrate through the porous portion and into the bone as the tissue regrows.

The plate also includes a suture anchor point disposed on the plate. The suture anchor point is configured to receive a free end of a suture so as to secure the suture to the plate after the suture has been sewn to the damaged tissue.

A method for repairing a torn tendon or ligament is also provided. The method includes the step of providing a plate. The plate includes a plurality of screw holes for accepting screws. One of the screw holes is a bone screw hole configured to receive a bone screw. The other screw holes is an anchor screw hole configured to receive anchor screws. The anchor screws include suture fixedly attached thereto.

The plate includes a porous portion surrounding the anchor screw holes. The porous portion is configured to allow muscle tissue to migrate through the porous portion and into the bone as the tissue regrows.

The plate also includes a suture anchor point disposed on the plate. The suture anchor point is configured to receive a free end of a suture so as to secure the suture to the plate after the suture has been sewn into the damaged tissue.

The method includes the step of securing the plate to a skeletal structure. In particular, a bone screw is inserted into the skeletal structure through the bone screw hole. The method includes the step of securing anchor screws to the skeletal structure through a respective anchor screw hole.

The method includes the step of sewing the suture to the torn muscle tissue, and securing the free end of the suture to the anchor point. The method may further include the step of providing a reinforcing mesh, wherein the reinforcing mesh is laid on top of the damaged muscle tissue and the sutures sew the muscle tissue to the reinforcing mesh.

In one aspect of the method, the free ends of the sutures are secured to the suture anchor point. In another aspect of the method, the reinforcing mesh is configured to attach directly to the suture anchor point. Accordingly, the plate and the method provide a secure anchor point for the sutures so as to mitigate the effects of osteoporosis or cystic changes.

BRIEF DESCRIPTION OF THE FIGURES

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

DETAILED DESCRIPTION OF THE EMBODIMENT

A plate for use in the repair of a torn tendon or ligament is provided. The plate includes a plurality of screw holes for accepting screws. The plate also includes a suture anchor point disposed on the plate. The plate further includes a porous portion configured to allow muscle tissue to migrate through the porous portion and into the bone as the tissue regrows.

A method for repairing a torn tendon or ligament is also provided. The method includes the step of providing the plate described in the above paragraph. The method includes the step of securing the plate to a bone by inserting a bone screw through on of the screw holes, and at least one anchor screw through the other of the screw holes, wherein the area of the plate surrounding the anchor screw is the porous portion.

The method proceeds to the step of sewing the sutures to the damaged tendon/ligament and securing the suture to the anchor point. Wherein the damaged tendon/ligament is attached to the plate, and wherein muscle tissue may migrate through the porous portion and into the bone as the tissue regrows.

Figure 1:
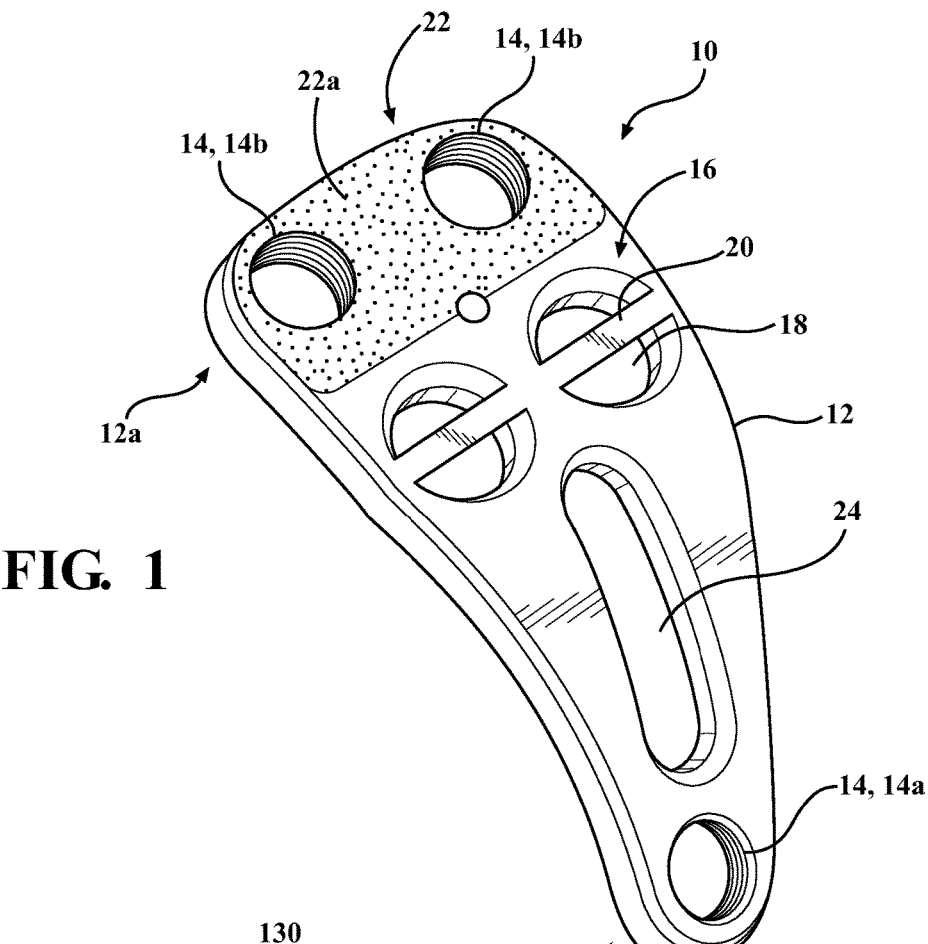
FIG. 1 shows an embodiment of a plate.

With reference now to FIG. 1, an illustrative view of the plate 10 is provided. The plate 10 has a plate body 12 which is illustratively shown as being tapered as viewed from the top down. The wide end 12a of the plate body 12 is bent relative to the narrow end 12b of the plate body 12 so as to accommodate the anatomy of a shoulder.

The plate body 12 may be made of PEEK, titanium, or other material acceptable for interbody use known to those skilled in the art. Accordingly, it should be appreciated by those skilled in the art that the shape of the plate body 12 may be dimensioned otherwise based upon the muscle tissue "T" being repaired. For illustrative purposes, the plate 10 will be described in relation to a rotator cuff repair procedure.

The plate 10 further includes a plurality of screw holes 14. For illustrative purposes the plate 10 is shown having three screw holes 14. Such an embodiment may be desirable for procedures commonly referenced as a double row procedure. One of the screw holes 14 is bone screw hole 14a. The bone screw hole 14a is configured to receive a bone screw 100. An illustrative example of a bone screw 100 is provided in FIG. 3. The bone screw 100 includes a head 100a having an engagement feature configured to cooperate with a screw driver (not shown) or other fastening tool. The bone screw 100 includes a shaft 100b having a thread 100c for anchoring into the skeletal structure 110 such as a bone.

Figure 2:
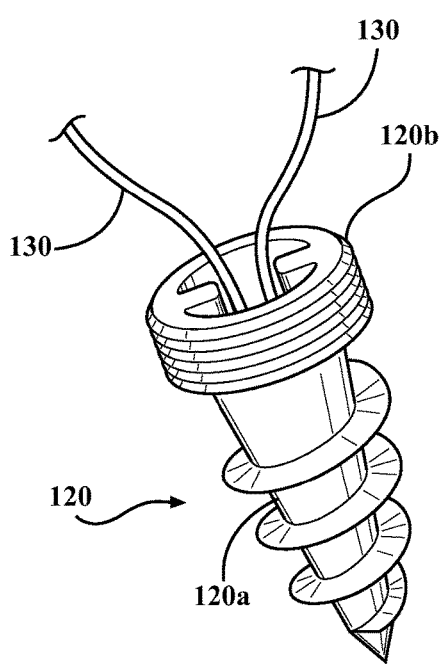
FIG. 2 shows an embodiment of an anchor screw.

The other two screw holes 14 are anchor screw holes 14b. As seen, the anchor screw holes 14b are disposed on the wide end 12a of the plate body 12. The anchor screw holes 14b may be threaded and are configured to receive an anchor screw 120. An illustrative example of an anchor screw 120 is provided in FIG. 2. The anchor screw 120 includes a threaded shaft 120a, and a threaded top end 120b. The threaded top end 120b is configured to threadingly engage a respective anchor screw hole 14b. The anchor screw 120 further includes a suture 130. One end of the suture 130 is fixed to the anchor screw 120. For illustrative purposes, the anchor screw 120 is shown having two sutures 130, however it should be appreciated by those skilled in the art that number of sutures 130 attached to a respective anchor screw 120 may be determined by the surgical procedure.

The plate 10 further includes a suture anchor point 16 disposed on the plate body 12. The suture anchor point 16 is configured to receive a free end of a suture 130 so as to secure the suture 130 to the plate 10 after the suture 130 has been sewn to the damaged tissue "T". For illustrative purposes the plate 10 is shown having two suture anchor points 16.

The suture anchor points 16 include an opening 18 and a crossing member 20 extending across the opening 18. The opening 18 allows the suture 130 to be wrapped around the crossing member 20 so as to secure the free end of a respective suture 130 to the plate body 12. Each of the openings 18 are opposite a respective anchor screw hole 14b and generally coaxially aligned with a respective anchor screw hole 14b.

The plate 10 includes a porous portion 22 surrounding the anchor screw holes 14b. The porous portion 22 includes a plurality of through-holes 22a so as to allow muscle tissue "T" to migrate through the porous portion 22 and into the bone as the tissue "T" regrows. The remaining plate body 12 may be formed of a non-porous material to inhibit bone growth.

The plate 10 may further include a screw slot 24. The screw slot 24 may extend along a longitudinal length of the plate body 12. The screw slot 24 is configured to receive a bone screw 100 so as to provide yet another attachment point. As seen the screw slot 24 is not threaded and thus is preferably provided for use with a non-locking screw.

Figure 3:
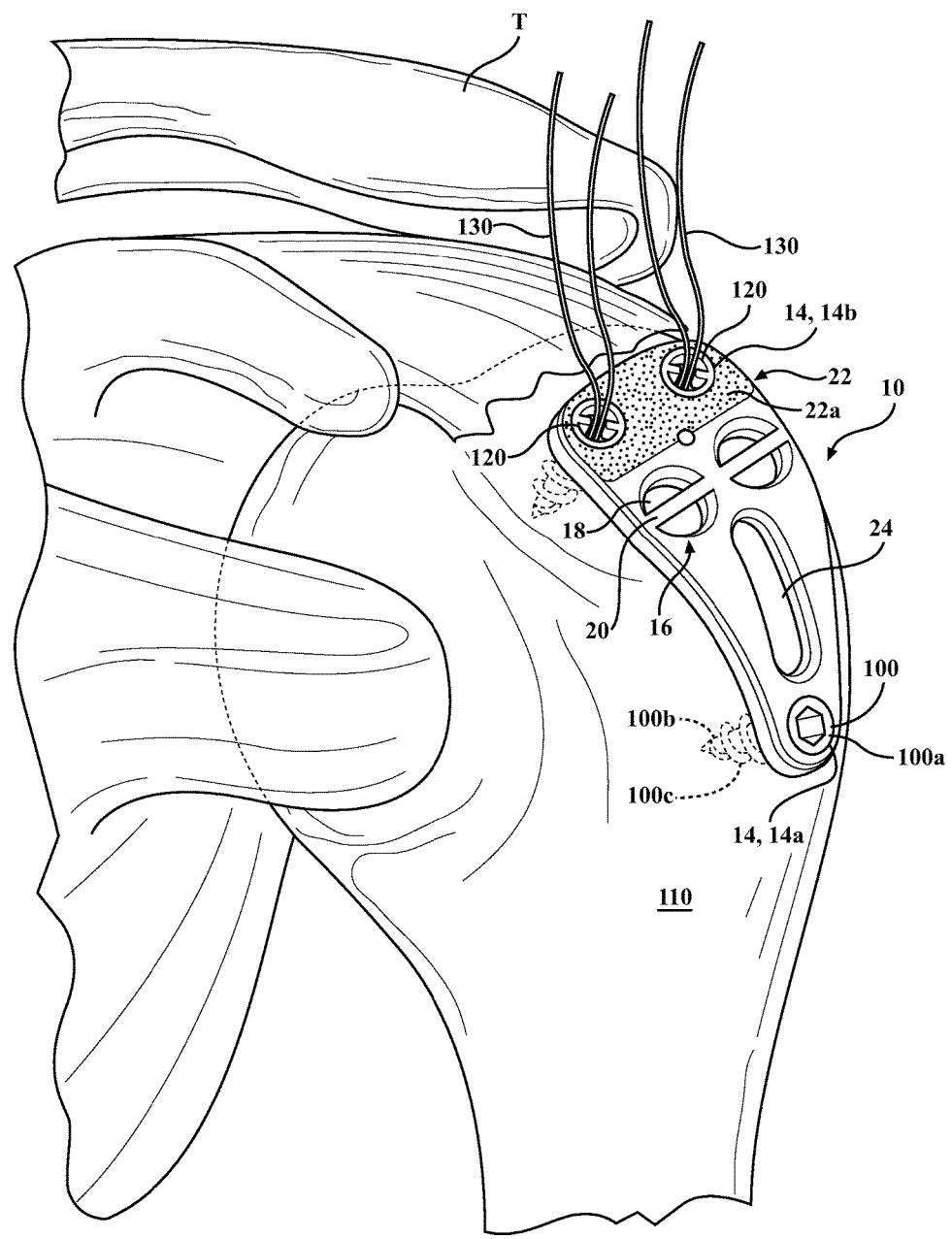
FIG. 3 shows the plate attached to a skeletal structure.
Figure 4:
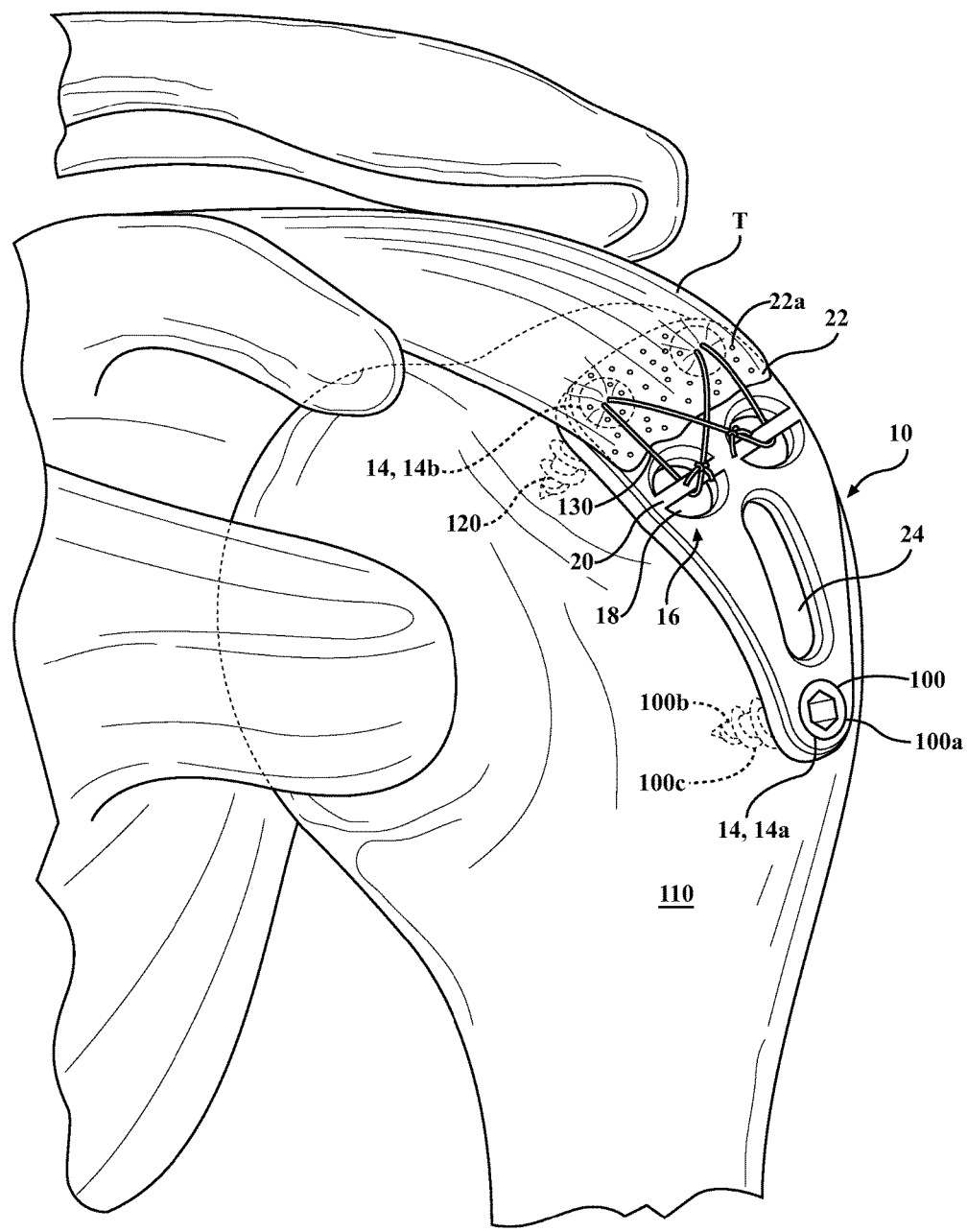
FIG. 4 shows the sutures sewn to muscle tissue and attached to the anchor point.

With reference now to FIGS. 3 and 4, a description of the use of the plate 10 is provided. FIG. 3 shows the plate 10 secured to a skeletal structure 110. In particular the plate 10 is secure to the proximal humerus bone. A bone screw 100 is passed through the bone screw hole 14a and into the proximal humerus bone, providing one point of attachment.

A pair of anchor screws 120 are attached to respective anchor screw holes 14b providing two other points of attachment. The sutures 130 may be seen extending freely from the plate body 12.

With reference now to FIG. 4, the sutures 130 have been sewn to the muscle tissue "T" (the rotator cuff) and secured to the suture anchor point 16. FIG. 4 shows a suture 130 from one anchor screw 120 being tied to a suture 130 from another anchor screw 120, however, it should be appreciated that the sutures 130 may be secured directly to a respective crossing member 20.

Figure 5:
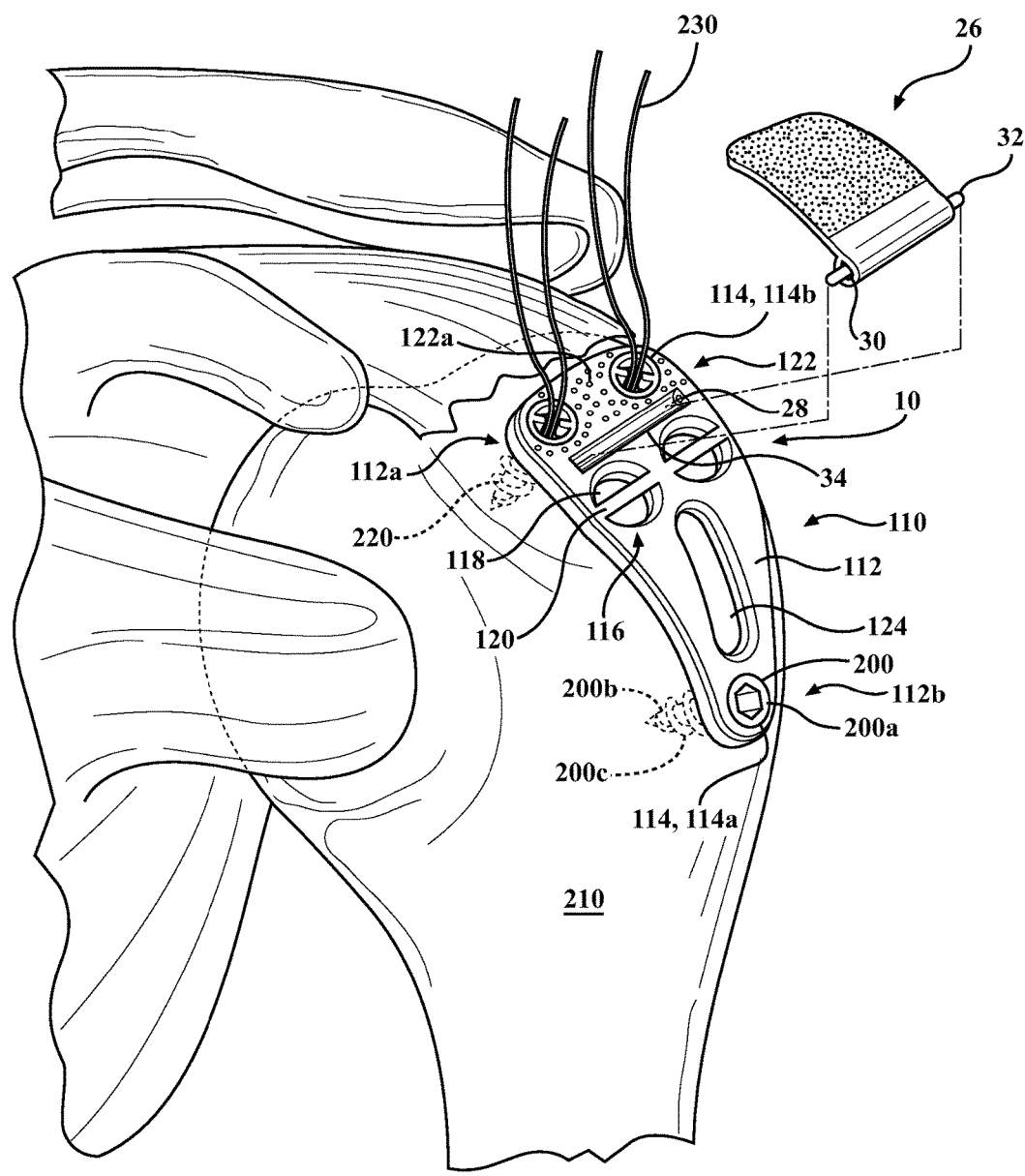
FIG. 5 shows a second aspect of the plate, configured for use with a reinforcing mesh.
Figure 6:
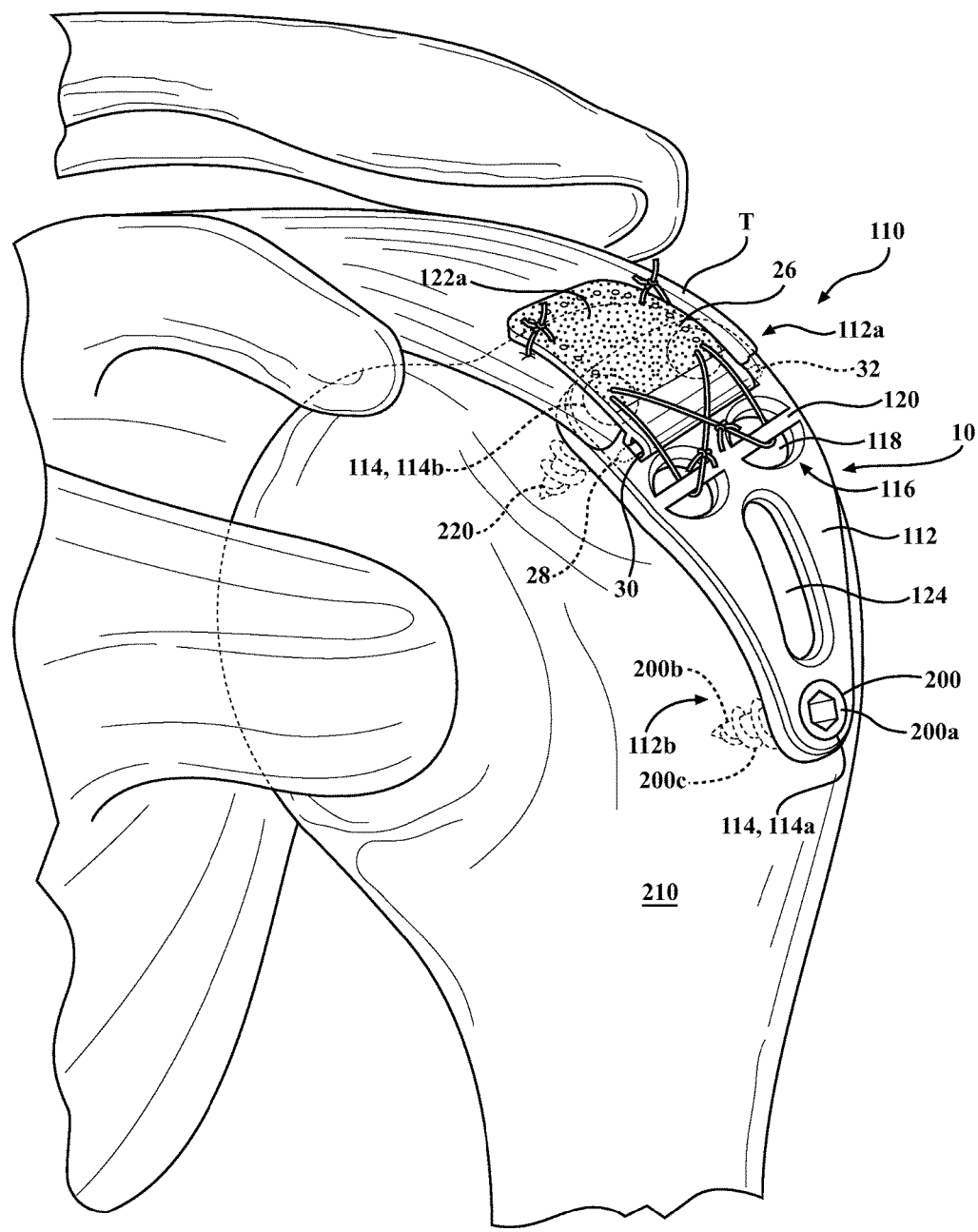
FIG. 6 shows the reinforcing mesh secure to the suture anchor point.

With reference now to FIGS. 5 and 6, a second aspect of the plate 110 is provided, wherein like elements are indicated by like reference numbers increased by 100. The plate 110 has a plate body 112. The plate body 112 may be made of PEEK, titanium, or other material acceptable for interbody use known to those skilled in the art. For illustrative purposes, the plate 110 will be described in relation to a rotator cuff repair procedure. However, it should be appreciated by those skilled in the art that the shape may be dimensioned otherwise based upon the muscle tissue "T" being repaired.

The plate 110 includes a plurality of screw holes 114. For illustrative purposes the plate 110 is shown having three screw holes 114. Such an embodiment may be desirable for procedures commonly referenced as a double row procedure. One of the screw holes 114 is bone screw hole 114a. The bone screw hole 114a is configured to receive a bone screw 200. An illustrative example of a bone screw 200 is provided in FIG. 5. The bone screw 200 includes a head having an engagement feature configured to cooperate with a screw driver or other fastening tool. The bone screw 200 includes a head 200a, and a shaft 200b. The shaft is threaded so as to anchor into the skeletal structure 210.

The other two screw holes 114 are anchor screw holes 114b. As seen, the anchor screw holes 114b are disposed on the wide end 112a of the plate body 112. The anchor screw holes 114b may be threaded and are configured to receive an anchor screw 220. An illustrative example of an anchor screw 220 is provided in FIG. 2. The anchor screw 220 includes a threaded shaft 220a, and a threaded top end 220b. The threaded top end 220b is configured to threadingly engage a respective anchor screw hole 114b. The anchor screw 220 further includes a suture 230. One end of the suture 230 is fixed to the anchor screw 220. For illustrative purposes, the anchor screw 220 is shown having two sutures 230, however it should be appreciated by those skilled in the art that number of sutures 230 attached to a respective anchor screw 220 may be determined by the surgical procedure.

The plate 110 further includes a suture anchor point 116 disposed on the plate body 112. In one aspect of the suture anchor point 116, the suture anchor point 116 is configured to receive a free end of a suture 230 so as to secure the suture 230 to the plate 110 after the suture 230 has been sewn into the damaged tissue "T". In another aspect of the suture anchor point 116, the suture anchor point 116 is configured to hold an end of a reinforcing mesh 26.

For illustrative purposes the plate 110 is shown both aspects of the suture anchor points 116. In the first aspect of the suture anchor point 116, the suture anchor point 116 include an opening 118 and a crossing member 120 extending across the opening 118. The opening 118 allows the suture 230 to be wrapped around the crossing member 120 so as to secure the free end of a respective suture 230 to the plate body 112.

In the second aspect of the suture anchor point 116, the suture anchor point 116 is shown having a retaining pin hole 28. The reinforcing mesh 26 is a pliable material that is porous. Any reinforcing mesh 26 currently known and used for surgical procedures may be adapted for use herein, illustratively including a reinforcing mesh 26 commonly referred to as "X-Repair Mesh", sold by Synthasome. The reinforcing mesh 26 includes a passage 30 disposed on one end of the reinforcing mesh 26. The passage 30 extends between opposite sides of the reinforcing mesh 26. A retaining pin 32 is disposed within the passage 30.

In the second aspect of the suture anchor point 116, the suture anchor point 116 includes an elongated groove 34 extending between opposite sides of the reinforcing mesh 26. The ends of the elongated groove 34 include the pin hole 28 configured to receive a respective end of the retaining pin 32. Accordingly, the reinforcing mesh 26 may be snapped into engagement within the elongated groove 34 by engagement of the ends of the retaining pin 32 into respective retaining pin holes 28.

Alternatively, the user may simply sew the sutures 130 to the tissue "T" and the reinforcing mesh 26 and secure the tissue "T" and reinforcing mesh 26 together by securing the suture 130 to the crossing member 20. FIG. 6, provides an illustrative view of a securement technique wherein the reinforcing mesh 26 is secured to the elongated groove 34 by snapping the retaining pins 32 into respective retaining pin holes 28, and the sutures 130 sew the tissue "T" to the reinforcing mesh 26. Sutures 130 secured to the anchor screw 220 may also be passed through the reinforcing mesh 26 also secured to the crossing members 20.

Figure 7:
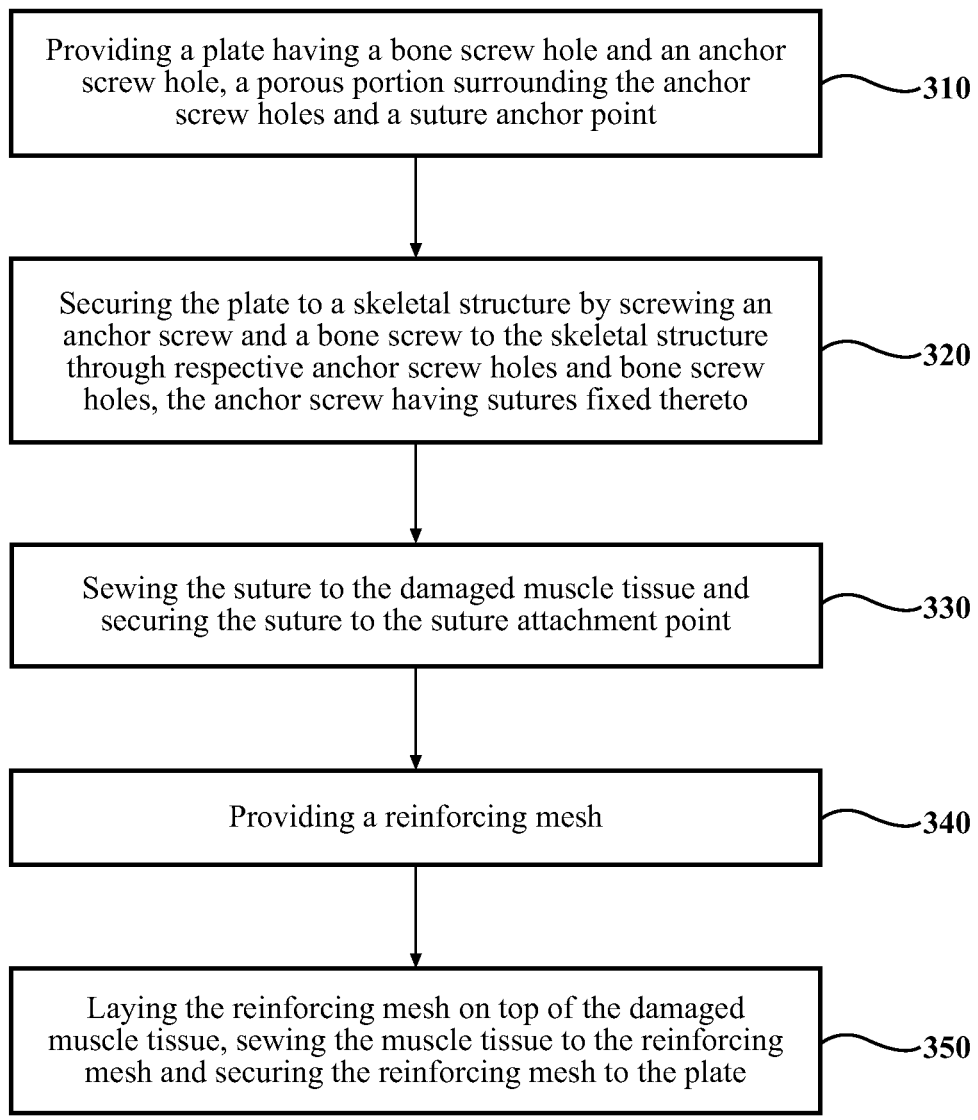
FIG. 7 is a diagram showing a method of repairing muscle tissue damage.

With reference now to FIG. 7 taken in view of FIGS. 4-6, a method 300 for repairing a damaged muscle tissue "T" is also provided. The method 300 includes step 310, providing a plate 10. The plate 10 includes a plurality of screw holes 14 for accepting screws 100, 120. One of the screw holes 14 is a bone screw hole 14a configured to receive a bone screw 100. The other screw holes 14 are an anchor screw hole 14b configured to receive anchor screws 110. The anchor screws 110 include suture 130 fixedly attached thereto.

The plate 10 includes a porous portion 22 surrounding the anchor screw holes 14b. The porous portion 22 is configured to allow muscle tissue "T" to migrate through the porous portion 22 and into the bone as the tissue "T" regrows. The plate 10 also includes a suture anchor point 16 disposed on the plate 10. The suture anchor point 16 is configured to receive a free end of a suture 130 so as to secure the suture 130 to the plate 10 after the suture 130 has been sewn into the damaged tissue "T".

The method includes step 320, securing the plate 10 to a skeletal structure. In particular, a bone screw 100 is inserted into the skeletal structure through the bone screw hole 14a, and anchor screws 110 are passed through the anchor screw holes 14b and secure the skeletal structure.

The method includes step 330, sewing the suture 130 to the damaged muscle tissue "T", and securing the free end of the suture 130 to the anchor point. The suture anchor point 16 includes an opening 18 and a crossing member 20 extending across the opening 18. The opening 18 allows the suture 130 to be wrapped around the crossing member 20 so as to secure the free end of a respective suture 130 to the plate body 12. Each of the openings 18 are opposite a respective anchor screw hole 14b and generally coaxially aligned with a respective anchor screw hole 14b.

The method may include step 340, providing a reinforcing mesh 26. The method may include step 350, laying the reinforcing mesh 26 on top of the damaged muscle tissue "T" and sewing the muscle tissue "T" to the reinforcing mesh 26 and securing the reinforcing mesh 26 to the plate 10. The reinforcing mesh 26 may include a passage 30 disposed on one end of the reinforcing mesh 26. The passage 30 extends between opposite sides of the reinforcing mesh 26. A retaining pin 32 is disposed within the passage 30.

The suture anchor point 16 may include an elongated groove 34 extending between opposite sides of the reinforcing mesh 26. The ends of the elongated groove 34 include a pin hole configured to receive a respective end of the retaining pin 32. Accordingly, the reinforcing mesh 26 may be snapped into engagement within the elongated groove 34.

Accordingly, in one aspect of the method 300, the free ends of the sutures 130 are secured to the suture anchor point 16. In another aspect of the method 300, the reinforcing mesh 26 is configured to attach directly to the suture anchor point 16. Accordingly, the plate 10 and the method 300 provide a secure anchor point for the sutures 130 so as to mitigate the effects of osteoporosis or cystic changes.

Figure 8:
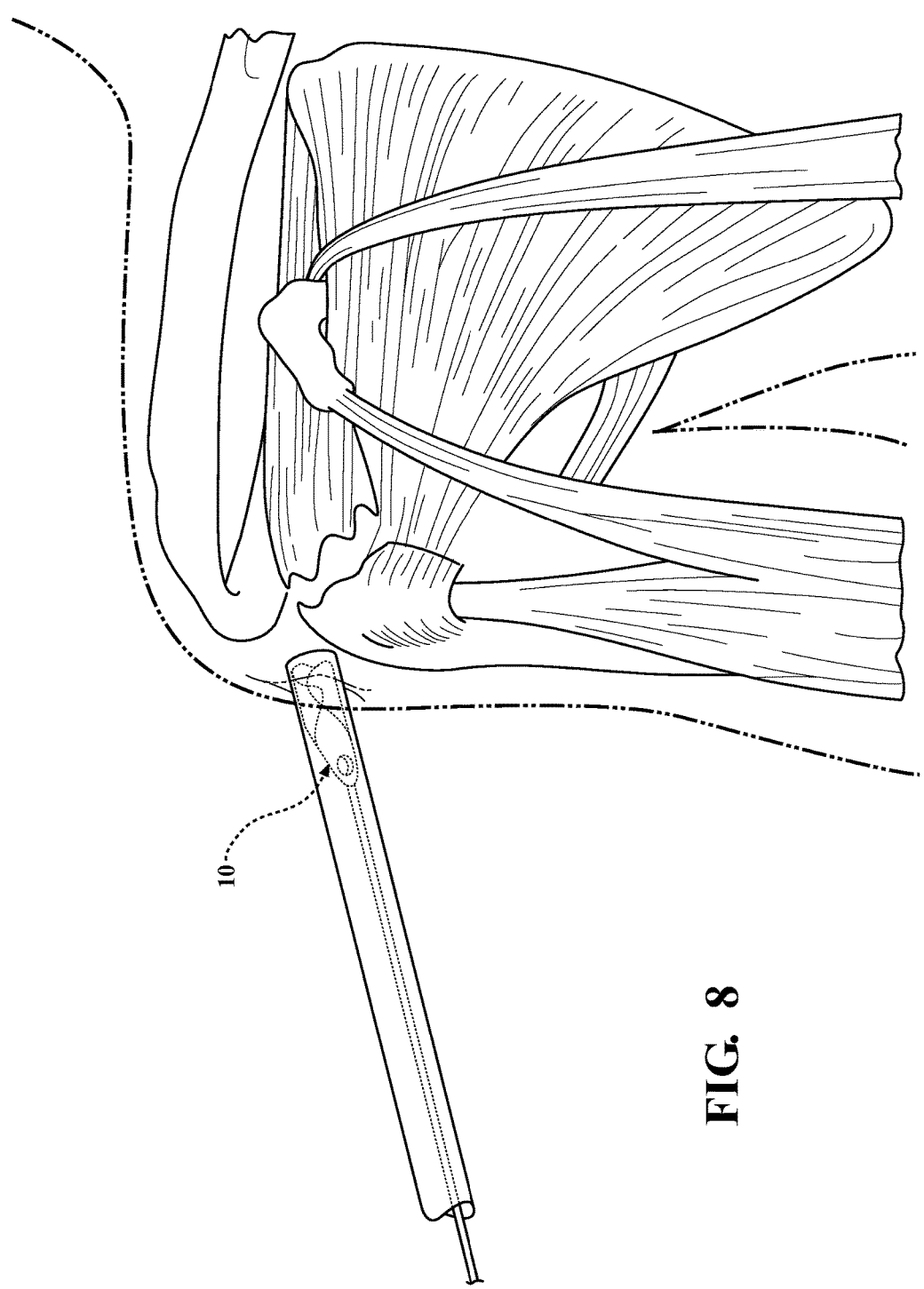
FIG. 8 shows a third aspect of the plate configured for use in an arthroscopic procedure.

With reference now to FIG. 8, the plate 10 may be used in an arthroscopic procedure, wherein the plate 10 is formed of a formable material approved for interbody use such as nitinol. In such an aspect, the plate 10 is provided in a rolled up state. The plate 10 may be passed through a surgical corridor to the surgical site. Upon reaching the surgical site, the plate 10 is unrolled so as to cover the bone, wherein the plate 10 is secure to the proximal humerus bone. A bone screw 100 is passed through the bone screw hole 14a and into the rotator cuff, providing one point of attachment.

A pair of anchor screws 110 are attached to respective anchor screw holes 14b providing two other points of attachment. The sutures 130 are sewn to the muscle tissue "T" and secured to the suture anchor point 16, as shown in FIG. 4. It should be appreciated that the reinforcing mesh 26 may also be used in conjunction with the plate 10 in an arthroscopic procedure.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

I claim:

1. A plate assembly for use in the repair of muscle tissue such as a torn tendon or ligament, the plate assembly comprising:
   a plate body having a plurality of screw holes, at least one hole being a threaded anchor screw hole, the plate body further having a porous portion, the porous portion surrounding at least one of the plurality of screw holes;
   a suture;
   a suture anchor point having a bar for receiving the suture disposed on the plate body; and
   at least one anchor screw, each anchor screw having shaft having a first threaded portion and a second threaded portion having a different thread from the first threaded portion, the first threaded portion adapted to be received in bone, the second threaded portion of the shaft, adapted to be threadably received in one of the threaded screw holes of the plate body, the second threaded portion having a center pocket for receiving the suture, the at least one anchor screw being spaced apart from the suture anchor point of the plate body such that the suture can be passed between the suture anchor point and the center pocket and over muscle tissue to secure the muscle tissue to the plate body.

2. The plate as set forth in claim 1, wherein one of the screw holes is a bone screw hole configured to receive a bone screw.

3. The plate assembly as set forth in claim 2, wherein the suture anchor point includes an opening and a crossing member extending across the opening.

4. The plate assembly as set forth in claim 3, wherein the porous portion of the plate body surrounds the anchor screw hole.

5. The plate assembly as set forth in claim 4, wherein the plate body includes a narrow end and a wide end, the narrow end being bent relative to the wide end.

6. The plate assembly as set forth in claim 5, wherein the anchor screw holes are disposed on the wide end of the plate body.

7. The plate assembly as set forth in claim 6, wherein the plurality of screw holes is a pair of threaded anchor screw holes and a single bone screw hole.

8. The plate assembly as set forth in claim 1, further including a reinforcing mesh, the reinforcing mesh configured to engage the suture anchor point.

9. The plate as set forth in claim 8, wherein the plate body includes an elongated groove having a pin hole on each end of the elongated groove, the reinforcing mesh having a passage, and a retaining pin disposed in the passage, wherein each end of the retaining pin is configured to engage a respective pin hole of the elongated groove so as to secure the reinforcing mesh to the suture anchor point.

* * * * *